United States Patent [19]
Butler

[11] Patent Number: 5,000,315
[45] Date of Patent: Mar. 19, 1991

[54] TAMPON

[76] Inventor: Sandra J. Butler, 233 Maribyrnong Avenue, Kaleen, A.C.T. 2617, Australia

[21] Appl. No.: 444,748

[22] Filed: Dec. 1, 1989

[51] Int. Cl.$^5$ .............................................. B65D 69/00
[52] U.S. Cl. ......................................... 206/229; 2/21; 604/904
[58] Field of Search ....................... 206/229, 38; 2/21; 604/904

[56] References Cited

U.S. PATENT DOCUMENTS

| | | | |
|---|---|---|---|
| 2,123,343 | 7/1938 | Rightsell | 2/21 |
| 2,438,901 | 4/1948 | Coxe | 2/21 |
| 2,637,031 | 5/1953 | Friedman | 2/21 |
| 2,701,878 | 2/1955 | Davis | 2/21 |
| 2,940,449 | 6/1960 | Thomson | 206/38 |
| 3,135,262 | 6/1964 | Kobler et al. | 604/904 |
| 3,263,681 | 8/1966 | Nechtow et al. | 2/21 X |

FOREIGN PATENT DOCUMENTS

| | | | |
|---|---|---|---|
| 120997 | 2/1946 | Australia | 2/21 |
| 269801 | 5/1965 | Australia | 604/904 |
| 64747 | 11/1982 | European Pat. Off. | 604/904 |
| 93641 | 3/1960 | Netherlands | 604/904 |
| 710670 | 6/1954 | United Kingdom | 604/904 |

*Primary Examiner*—William I. Price
*Attorney, Agent, or Firm*—Kane, Dalsimer, Sullivan, Kurucz, Levy, Eisele and Richard

[57] ABSTRACT

A packaged tampon 19 of the kind comprising a body of absorbent material intended for internal use in a body cavity to absorb blood, body secretions and the like, is enclosed in its own individual outer covering 17 and a disposable fingerstall 13 made of thin, flexible material such as polyethylene is also enclosed within the outer covering 17, said fingerstall 13 being adapted to cover the finger used to position the tampon in the body cavity. A method and an apparatus for producing a packaged tampon is also described.

7 Claims, 2 Drawing Sheets

TAMPON

FIELD OF INVENTION

The invention relates to a tampon of the kind comprising a pad or plug or the like of absorbent material which may be used in a body cavity for the absorption of blood, body secretions and the like. In particular, the invention concerns a tampon of the kind which is intended for the purposes of female hygiene and which may be used internally to absorb menstrual flow.

DESCRIPTION OF THE PRIOR ART

A tampon of this kind may be formed as a somewhat cylindrical plug of cotton, sponge, or other absorbing material. It should be sufficiently strong to retain its shape while it is being inserted to its correct position in the body cavity but sufficiently flexible to permit insertion to be performed comfortably. It is important that such a tampon is inserted correctly and for a sufficient distance. Generally, a tampon is inserted manually being held, for example, by the thumb and second finger and positioned by gently pushing it in by the index finger to the full length thereof. If the tampon is not correctly positioned, the process may have to be repeated using a fresh tampon. Many women find this process of insertion distasteful, and are discouraged from using tampons.

There are hygiene problems associated with this kind of tampon. For example, tampon use has been associated with a disease known as Toxic Shock Syndrome. This disease is thought to be caused by bacterial infection and may have serious consequences. To minimise risk, tampons are usually sold in a package wherein each tampon is also individually wrapped or provided with its own container. It is generally recommended that a tampon is not unwrapped or removed from its container until immediately before insertion and that it should not be handled more than is absolutely necessary.

Thorough washing of hands immediately before and after inserting a tampon is strongly recommended. This is essential due, firstly, to the handling requirements of tampons and, secondly, because of the manual insertion techniques. In regard to this latter matter, there is not only a risk of infection by insertion of a finger, there is also a risk of matter being deposited under a fingernail, particularly in the case of a person with long fingernails.

These hygiene problems are amplified because it is recommended that tampons should be changed frequently, for example, at least three or more times a day. Thus, for many women, tampon changes must be made away from the privacy of the home and its associated facilities.

BRIEF SUMMARY OF INVENTION

It is an object of the invention to minimise these problems.

It is another object of the invention to make the use of tampons more hygienic.

To this end, for each tampon, it is proposed to provide at least one fingerstall to cover and protect the finger used to push the tampon into position in a body cavity.

According to the invention, there is provided a packaged tampon of the kind comprising a body of absorbent material intended for internal use in a body cavity to absorb blood, body secretions and the like, said tampon being enclosed in its own individual outer covering, characterised in that a disposable finger-stall made of thin, flexible material is also enclosed within said outer covering, said fingerstall being adapted to cover the finger used to position the tampon in the body cavity. Thus, an aseptic tampon and fingerstall are provided within the outer protective covering.

Because the fingerstall is intended to be disposable, it should be capable of low cost production so that it is economic to dispose of it after a single use.

Preferably, a fingerstall is in the form of a tubular sheath, closed at one end and open at the other. The length of a fingerstall should be a little longer than finger length so that it will completely enclose any finger used to push the tampon into its correct position. The diameter of the tubular sheath may be a little greater than that of a finger to provide a relatively close fitting cover for the finger so that the fingerstall is unlikely to be removed accidentally from the finger when it is in use. Alternatively, a looser fitting fingerstall may be used, in which case the open end of the tubular sheath, or an intermediate portion thereof, may be made so that it tightly grips the finger to ensure that the fingerstall does not accidentally come off during use.

A fingerstall should be flexible, not only because of its use as a fingerstall during tampon insertion, but also to facilitate packaging. An elastic material is preferred.

The material from which the fingerstall is made should be thin enough so as not to dull the wearer's perception by touch. It should be a smooth material so as to minimise the risk of irritation of delicate internal body tissue.

For hygiene reasons, a fingerstall should be impervious to fluids likely to be encountered in use during insertion of the tampon and should be such as to minimise the risk of transmission of infection. The material from which the fingerstall is made should be of such strength that it is unlikely to rupture during use.

A fingerstall made of thin rubber-like material or thin plastics material such as polyethylene meets these criteria. Such a fingerstall is not only comfortable during the insertion process but also promotes confidence and assists correct placement of the tampon by feel and touch. Preferably, the fingerstall material is also biodegradable.

Preferably, the fingerstall is packed so as to afford additional protection for the tampon. It may be wound around the tampon so that the volume of the tampon is not materially increased. Mechanical means may be employed to wind a fingerstall around a tampon. The combined fingerstall and tampon may then be placed into a container such as a bubble pack of plastics material, or may be individually wrapped, using existing equipment. The fingerstall wound in this manner assists hygiene as it may be left in position to minimise exposure of the tampon until the moment of insertion.

In a preferred form, a flattened fingerstall is temporarily attached to the internal surface of the covering material as a preliminary step in the packaging process.

In another form, a tampon may be inserted into a fingerstall and enclosed in individual coverings as described above.

The invention also comprises a method and apparatus for producing a packaged tampon.

BRIEF DESCRIPTION OF THE DRAWINGS

To further illustrate the invention, one embodiment thereof will now be described in relation to the accompanying drawings in which.

DETAILED DESCRIPTION

Figure 1:
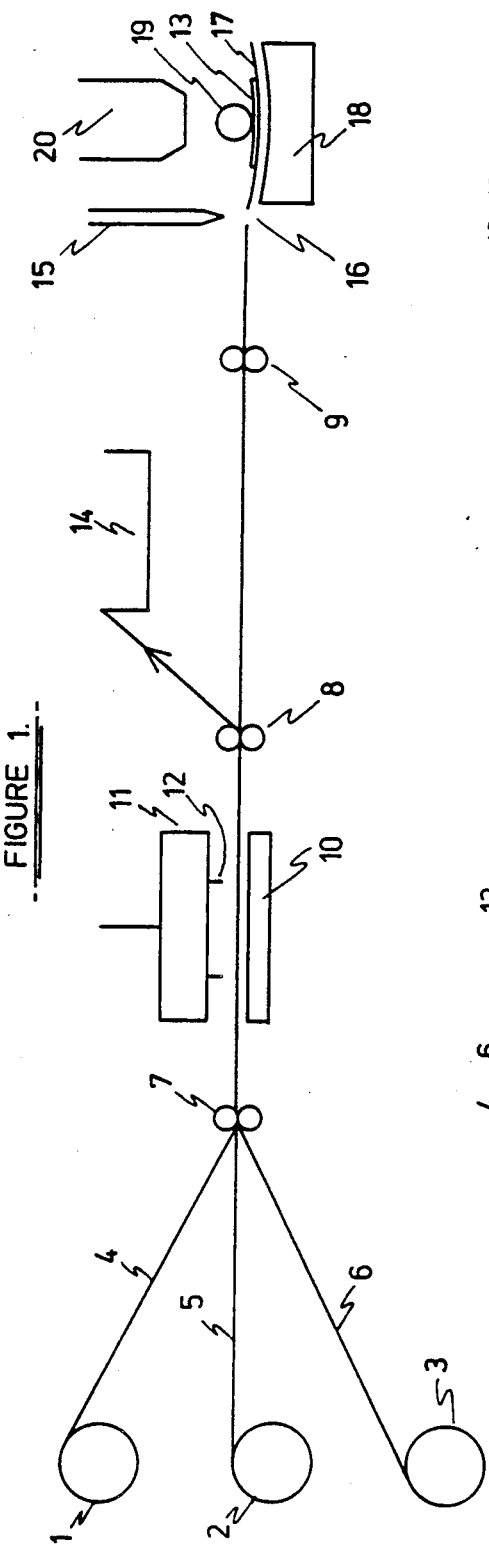
FIG. 1 is a schematic view of an apparatus capable of forming a packaged tampon.
Figure 2:
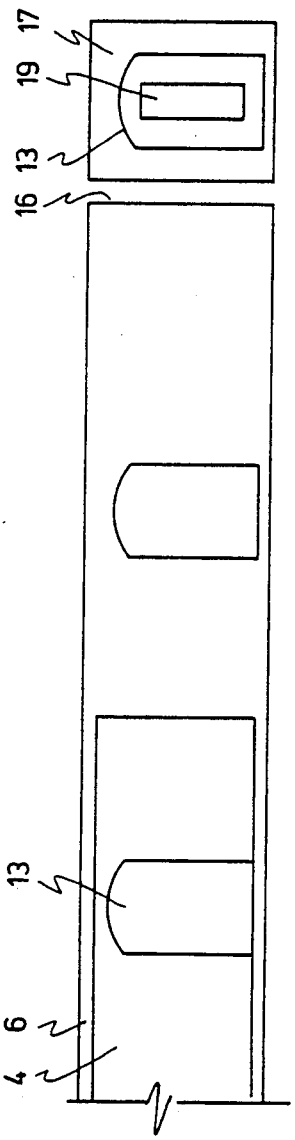
FIG. 2 is a plan view of the web of covering material illustrating various stages of manufacture employing the apparatus of FIG. 1.

In the apparatus illustrated in FIG. 1, there are three rolls 1, 2 and 3 supplying two continuous webs 4 and 5 of thin plastics material such as polyethylene and a continuous web 6 of paper of a kind suitable for forming a wrapper for a tampon. Webs 4 and 5 have the same width which is a little larger than the length of the fingerstall to be formed. Web 6 is wider than webs 4 and 5 and extends outwardly thereof on both sides.

The three webs are aligned vertically and are brought together between transverse feed rollers 7. The composite web then travels horizontally between other transverse feed rollers 8 and 9 and through several work positions spaced along the path of the composite web. The feed rollers are intermittently driven in unison to move the composite web along its path, periods of movement being alternated with periods in which the web is held stationary to allow work to be performed at the several work positions.

At the first work position past transverse feed rollers 7, the composite web passes over backing member 10 which is situated below a vertically movable cutting and sealing member 11 carrying a thin steel die 12 with a rounded cutting edge, die 12 being shaped in the outline of fingerstall 13.

With composite web stationary, heated die 12 is moved downwardly to impress momentarily on the composite web. In doing so, it performs three functions. Firstly, die 12 by its heat cuts plastic sheets 4 and 5 along the outline of fingerstall 13 without damaging paper web 6 by cutting or burning although the paper is slightly embossed. Embossment is facilitated by providing backing member 10 with the yielding upper surface. Secondly, die 12 by heat sealing joins plastic sheets 4 and 5 along the edges formed by the cut. The seal is very narrow and extends completely to the cut edges so that the join is not noticable and a smooth external surface results. The mouth of the fingerstall is formed by the unjoined portions at one edge of webs 4 and 5. Thirdly, the heat of die 12 and the embossment of paper web 6 is effective to attach fingerstall 13 at its free edges to paper web 6. Thus, fingerstall 13 is retained in place on paper web 6 for the remainder of the wrapping process but is easily separated therefrom when the wrapped tampon is opened.

Any suitable means such as electrical heating means may be employed to heat die 12 to a temperature above that required to cut the plastic sheets and seal their free edges but below that which would cause burning of paper web 6. A temperature of about 250° C. would be suitable. Similarly, any suitable means may be used to move die 12 downwardly to momentarily impress the composite web and then move die 12 upwardly. The pressure of die 12 on the composite web should be sufficient to emboss paper web 6 but not enough to cause tearing or cutting thereof.

After the composite web passes between transverse drive rollers 8, the waste plastic which does not form part of the fingerstalls 13 is removed from the upper surface of paper web 6 by any suitable means and transferred to a waste container 14.

Figure 3:
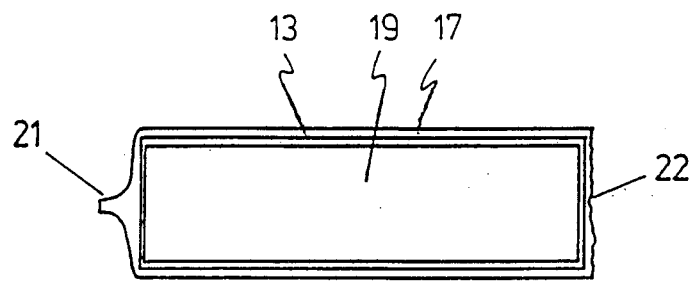
FIG. 3 is a sectional view of a wrapped tampon and fingerstall.

The resulting paper web 6, which has fingerstalls 13 attached thereto at spaced intervals, is then passed between transverse drive rollers 9 to transverse knife 15 which may be moved downwards to cut paper web 6 along a transverse line 16 between fingerstalls 13 and then moved upwards. The separated paper wrapper 17 with a fingerstall 13 attached is received at a wrapping position 18 and a tampon 19 is released from hopper 20 and is deposited on fingerstall 13. The tampon may be provided with a cord (not shown) attached at one end thereof to assist withdrawal from a body cavity. Wrapping and sealing of tampon 19, which may be effected in the usual way, causes fingerstall 13 to be wrapped around tampon 19. A wrapped tampon 19 and fingerstall 13 is illustrated in FIG. 3. At one end, wrapper 17 is formed with an outward projection 21 which may be torn to open the wrapper. The other end 22 may be flat. Alternatively, both ends may be flat and the usual type of tear strip provided.

Movement of die 12 and knife 15 and operation of the wrapper mechanisn are synchronized with the operation of drive rollers 7, 8 and 9 to take place when the composite web is stationary.

Various modifications may be made to the apparatus and method described. For example, instead of two rolls of plastic sheet material, a double sheet may be wound upon a single roll. Paper web 6 may have its upper surface prepared to assist the temporary attachment of fingerstall 13 thereto. It is preferred to include means to clean and/or lubricate die 12 so that it does not stick to the plastic sheets 4 and 5. Additional steps may also be included in the basic process described. For example, a lubricating step may be included whereby a material such as talcum powder is inserted into fingerstall 13. Another example is the inclusion of a sterilizing step after the tampon 19 has been deposited on fingerstall 13.

The method and apparatus described is amenable to high speed mass production of a packaged tampon and fingerstall at a cost not significantly greater that that required in the present wrapping of a tampon.

Figure 4:
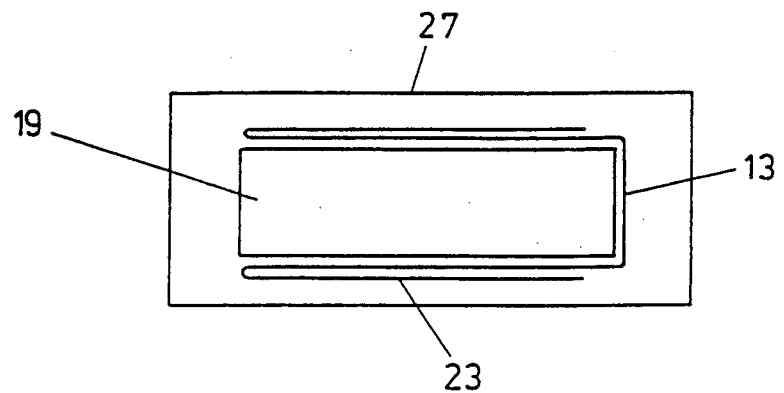
FIG. 4 is a sectional view of a tampon and fingerstall packaged in a container.

Various other modifications may be made to the fingerstall, the package, the individual wrappings or containers, the manner in which the tampon and fingerstall are associated and the materials employed. For example, the tampon with its fingerstall may be enclosed within a container 27 such as a bubble pack of plastics material. The containers may be separate from one another or joined together in strip form. The tampon 19 may be located in the fingerstall 13 which may be rolled over on itself as shown at 23 in FIG. 4 and may be pushed from the fingerstall by pressure on its inner end as the fingerstall is being fitted over a finger. It is thus possible to insert a tampon into position in a body cavity, without it being handled.

More than one fingerstall may be included in each container or wrapping. Alternatively, a package of individually wrapped or containerised tampons may include additional fingerstalls individually wrapped in paper or plastic envelopes.

By employing the principles described, an aseptic tampon and fingerstall are conveniently provided, the fingerstall affording additional protection for the tampon.

I claim:

1. A packaged tampon of the kind comprising a body of absorbent material intended for internal use in a body cavity to absorb blood, body secretions and the like, said tampon being enclosed in its own individual outer covering, characterised in that a disposable fingerstall in the form of a tubular sheath, closed at one end and open at the other, and made of thin, flexible, rubber-like or plastics material which is impervious to blood and other body secretion, is also enclosed within said outer covering, said fingerstall being adapted to completely cover the finer used to position the tampon in the body cavity.

2. A packaged tampon as claimed in claim 1, wherein said tampon comprises a substantially cylindrical plug of absorbent material.

3. A packaged tampon as claimed in claim 1, wherein the material from which the finerstall is made is of such strength that it is unlikely to rupture during use.

4. A packaged tampon as claimed in claim 1, wherein the material from which the finerstall is made is polyethylene.

5. A packaged tampon as claimed in claim 1, wherein the fingerstall is in a substantially flattened form and is temporarily attached to the internal surface of the outer covering.

6. A packaged tampon as claimed in claim 1, wherein the fingerstall is wound around the tampon.

7. A packaged tampon as claimed in claim 1, wherein the tampon is positioned within the fingerstall.

* * * * *